United States Patent
Sasada (10) Patent No.: US 7,433,537 B2
(45) Date of Patent: Oct. 7, 2008

(54) IMAGE REPRODUCTION SYSTEM FOR REMOVING NOISE OF A PERIODIC PATTERN

(75) Inventor: Ryoji Sasada, Kaisei-machi (JP)

(73) Assignee: FUJIFILM Corporation, Tokyo (JP)

( * ) Notice: Subject to any disclaimer, the term of this patent is extended or adjusted under 35 U.S.C. 154(b) by 644 days.

(21) Appl. No.: 10/170,562

(22) Filed: Jun. 14, 2002

(65) Prior Publication Data

US 2002/0191829 A1    Dec. 19, 2002

(30) Foreign Application Priority Data

Jun. 19, 2001 (JP) .............................. 2001-184420

(51) Int. Cl.
  *G06K 9/40* (2006.01)
  *G06K 9/00* (2006.01)
  *G06K 9/48* (2006.01)
  *H04N 13/00* (2006.01)

(52) U.S. Cl. ................... 382/275; 382/128; 382/198; 378/44

(58) Field of Classification Search ................ 382/260, 382/295, 268, 298–300, 128–132, 274–275; 378/44–54, 62–64
See application file for complete search history.

(56) References Cited

U.S. PATENT DOCUMENTS

| 4,258,264 A | 3/1981 | Kotera et al. |
| 4,276,473 A | 6/1981 | Kato et al. |
| 4,315,318 A | 2/1982 | Kato et al. |
| 5,028,784 A | 7/1991 | Arakawa et al. |
| 6,052,487 A | 4/2000 | Ito |
| 6,201,249 B1 * | 3/2001 | Yamayoshi ............ 250/370.11 |
| 6,285,781 B1 | 9/2001 | Yamazaki |
| 2001/0033638 A1 | 10/2001 | Inoue |

FOREIGN PATENT DOCUMENTS

| EP | 1 120 743 | 1/2001 |
| JP | 55-12429 | 1/1980 |
| JP | 55-163472 | 12/1980 |
| JP | 56-11395 | 2/1981 |
| JP | 55-116340 | 6/1981 |
| JP | 56-164645 | 12/1981 |
| JP | 03-114039 | 5/1991 |
| JP | 6-130516 | 5/1994 |
| JP | 10-262961 | 10/1998 |
| JP | 2000-11174 | 1/2000 |
| JP | 2001-212119 A | 8/2001 |

OTHER PUBLICATIONS

U.S. Appl. No. 09/765,621 filed on Jan. 22, 2001.
Japanese Office Action dated Aug. 21, 2007.

* cited by examiner

*Primary Examiner*—Bhavesh Mehta
*Assistant Examiner*—Manav Seth
(74) *Attorney, Agent, or Firm*—Sughrue Mion, PLLC (57) ABSTRACT

An original image data representing an image read out from an original is removed with noise of a predetermined periodic pattern, if any, and storage image data is generated. The storage image data is stored in an image memory and is subjected to an enlargement/reduction processing and output image data is generated. An image is reproduced on the basis of the output image data.

9 Claims, 5 Drawing Sheets

IMAGE REPRODUCTION SYSTEM FOR REMOVING NOISE OF A PERIODIC PATTERN

BACKGROUND OF THE INVENTION

1. Field of the Invention

This invention relates to an image reproduction system which outputs a reproduction image on the basis of original image data obtained by reading out an original image recorded on a recording medium (photographic film, paper or the like).

2. Description of the Related Art

There has been put into practice in various fields an image reproduction system which outputs a reproduction image through a printer or the like on the basis of original image data obtained by reading out an original image recorded on a recording medium (photographic film, paper or the like) by the use of an image scanner or the like.

When certain kinds of phosphor are exposed to a radiation (x-rays, α-rays, β-rays, electron beams, ultraviolet rays), they store a part of energy of the radiation. Then when the phosphor which has been exposed to the radiation is exposed to stimulating rays such as visible light, light is emitted from the phosphor in proportion to the stored energy of the radiation. A phosphor exhibiting such properties is generally referred to as "a stimulable phosphor". In this specification, the light emitted from the stimulable phosphor upon stimulation thereof will be referred to as "stimulated emission". In the medical field, there has been known a radiation image recording/reproducing system in which a stimulable phosphor sheet (a sheet provided with a layer of the stimulable phosphor) is exposed to a radiation passing through an object such as a human body to have a radiation image of the object stored on the stimulable phosphor sheet, stimulating light beam such as a laser beam is caused to scan the stimulable phosphor sheet bearing thereon the radiation image of the object, the stimulated emission emitted from the stimulable phosphor sheet upon exposure to the stimulating light is photoelectrically detected, thereby obtaining a radiation image signal, and then a radiation image of the object is reproduced on the basis of the radiation image signal as a visible image on a recording medium such as a photographic film or a display such as a CRT. See, for instance, Japanese Unexamined Patent Publication Nos. 55(1980)-12429, 56(1981)-11395, 55(1980)-163472, 56(1981)164645 and 55(1980)-116340.

When recording a radiation image of an object on a recording medium such as the stimulable phosphor sheet, a grid in which linear members of a radiation-untransmissible material (a material which is very low in permeability to the radiation) such as lead and linear members of a radiation-transmissible material (a material which is high in permeability to the radiation) such as aluminum or wood are alternately arranged at fine pitches of about 4/mm is sometimes interposed between the object and the stimulable phosphor sheet in order to prevent the stimulable phosphor sheet from being exposed to the radiation scattered by the object. By the use of such a grid, exposure of the stimulable phosphor sheet to the radiation scattered by the object is suppressed and the contrast of the radiation image of the object is enhanced. However, when a radiation image including therein an image of the grid is enlarged or reduced, aliasing is caused due to fold according to the rate of enlargement or reduction. Further, if the aliasing is superposed on the spatial frequency of, for instance, a grid image, fine moiré fringes are generated, which deteriorates quality of the reproduced image.

In view of these conditions, this applicant has proposed an image signal generating device which obtains an image signal, on the basis of which an image having less moire fringes and less aliasing can be reproduced, by carrying out on the image signal a filtering processing for removing spatial frequency components of the grid image (Japanese Unexamined Patent Publication No. 3(1991)-114039) and a grid removing device which extracts spatial frequency components of the grid image by the use of, for instance, Wavelet transform and removes them (Japanese Patent Application No. 2000-11174).

However, the grid removing devices such as described above for removing spatial frequency components according to the grid image generally may be installed in one of a radiation image read-out apparatus, an image processing apparatus connected downstream of a radiation image read-out apparatus and an image output apparatus (a monitor or a printer). Accordingly, when the grid removing device is installed in an image output means, it is natural that an image output from an image output means provided with a grid removing device is free from a grid image but an image output from an image output means not provided with a grid removing device cannot be free from a grid image. However, installing the grid removing device in all of the radiation image read-out apparatus, the image processing apparatus and the image output apparatus results in increase in cost and waste of the grid removing devices which are not actually used

SUMMARY OF THE INVENTION

In view of the foregoing observations and description, the primary object of the present invention is to provide an image reproduction system in which an image signal free from the grid image which generates moiré fringes can be constantly output even if it is output from any one of different image output means.

In accordance with a first aspect of the present invention, there is provided an image reproduction system comprising an image output means which outputs a reproduced image on the basis of an original image data representing an image read out from an original, wherein the improvement comprises that there are provided a periodic pattern removing means which carries out on the original image data a noise removing processing to remove noise of a predetermined periodic pattern from the original image data and generates storage image data, an image storage means which stores the storage image data and an output image processing means which carries out an enlargement/reduction processing on the storage image data read out from the image storage means and generates output image data, and the image output means outputs a reproduced image on the basis of the output image data.

In accordance with a second aspect of the present invention, there is provided an image reproduction system comprising an image output means which outputs a reproduced image on the basis of an original image data representing an image read out from an original, wherein the improvement comprises that there are provided a periodic pattern removing means which carries out on the original image data a noise removing processing to remove noise of a predetermined periodic pattern from the original image data and generates processed original image data, a storage image processing means which generates storage image data by converting the processed original image data to storage image data whose resolution is lower than that of the processed original image data, an image storage means which stores the storage image data and an output image processing means which carries out an enlargement/reduction processing on the processed original image data and/or the storage image data and generates output image data, and the image output means outputs a reproduced image on the basis of the output image data.

The original image data need not always has noise of the predetermined periodic pattern, and the noise removing section may remove noise of the predetermined periodic pattern only when the original image data includes therein noise of the predetermined periodic pattern.

The "noise of the predetermined periodic pattern" means a noise having a periodic pattern and may be, for instance, image data components representing a grid image which are included in the original image data when a radiation image is taken by the use of said grid.

The term "enlargement/reduction processing" should be broadly interpreted to include enlargement or reduction at a rate of 1.

"Converting the processed original image data to storage image data whose resolution is lower than that of the processed original image data" in the image reproducing system in accordance with the second aspect of the present invention means, for instance, to lower the pixel density of the processed original image data by carrying out a reduction processing on the processed original image data.

In the image reproducing system in accordance with the first and second aspects of the present invention, the image output means may comprise an image recording section which reproduces as a hard copy recorded on a predetermined recording medium an image on the basis of the output image data, and an image display section which displays as display an image on the basis of the output image data.

The image recording section may comprise, for instance, a printer and the image display section may comprise, for instance, a monitor.

The original image data may be provided with imaging menu information and the periodic pattern removing means may carry out a noise removing processing on the original image data according to the imaging menu represented by the imaging menu information.

The "imaging menu information" means, for instance, information on the object part, e.g., hand, foot or breast when the original image is a radiation image. The expression "the periodic pattern removing means carries out a noise removing processing on the original image data according to the imaging menu represented by the imaging menu information" means that, for instance, when the object part is a hand or foot, the periodic pattern removing means carries out no noise removing processing since no grid is used in taking a radiation image in such a case, when the object part is a lumber, the periodic pattern removing means carries out a noise removing processing for removing a vertical grid image since a vertical stationary grid is used in taking a radiation image in such a case, and when the object part is a pelvis, the periodic pattern removing means carries out a noise removing processing for removing a horizontal grid image since a horizontal stationary grid is used in taking a radiation image in such a case. When the object part is a part an image of which is rarely taken, the periodic pattern removing means carries out a noise removing processing on the basis of the result of automatic grid image recognition.

In the image reproduction system in accordance with the first aspect of the present invention, the original image data is removed with noise of periodic pattern to generate storage image data, the storage image data is stored in the image storage means, output image data is generated by carrying out an enlargement/reduction processing on the storage image data read out from the image storage means and a reproduced image is output on the basis of the output image data. Accordingly, an image free from moiré fringes can be constantly reproduced even if it is output from any one of different image output means. Further, the periodic noise removing means can be common to a plurality of different image output means, which results in reduction of cost.

In the image reproduction system in accordance with the second aspect of the present invention, the original image data is removed with noise of periodic pattern to generate processed image data, storage image data is generated by converting the processed original image data to storage image data whose resolution is lower than that of the processed original image data and is stored in the image storage means, output image data is generated by carrying out an enlargement/reduction processing on the processed original image data and/or the storage image data, and a reproduced image is output on the basis of the output image data. Accordingly, the amount of the storage image data can be reduced, whereby the image storage means can be small incapacity, and at the same time, the storage image data can be transferred at high speed. Such features can be obtained in addition to the features obtained in the image reproducing system of the first aspect.

When the original image data is provided with imaging menu information and the periodic pattern removing means carries out a noise removing processing on the original image data according to the imaging menu represented by the imaging menu information, a more proper noise removing processing can be carried out on the original image data so that information other than noise can be suppressed from being lost by the noise removing processing.

DESCRIPTION OF THE PREFERRED EMBODIMENT

A radiation image reproducing system in accordance with a first embodiment of the present invention will be described with reference to FIG. 1, hereinbelow.

Figure 1:
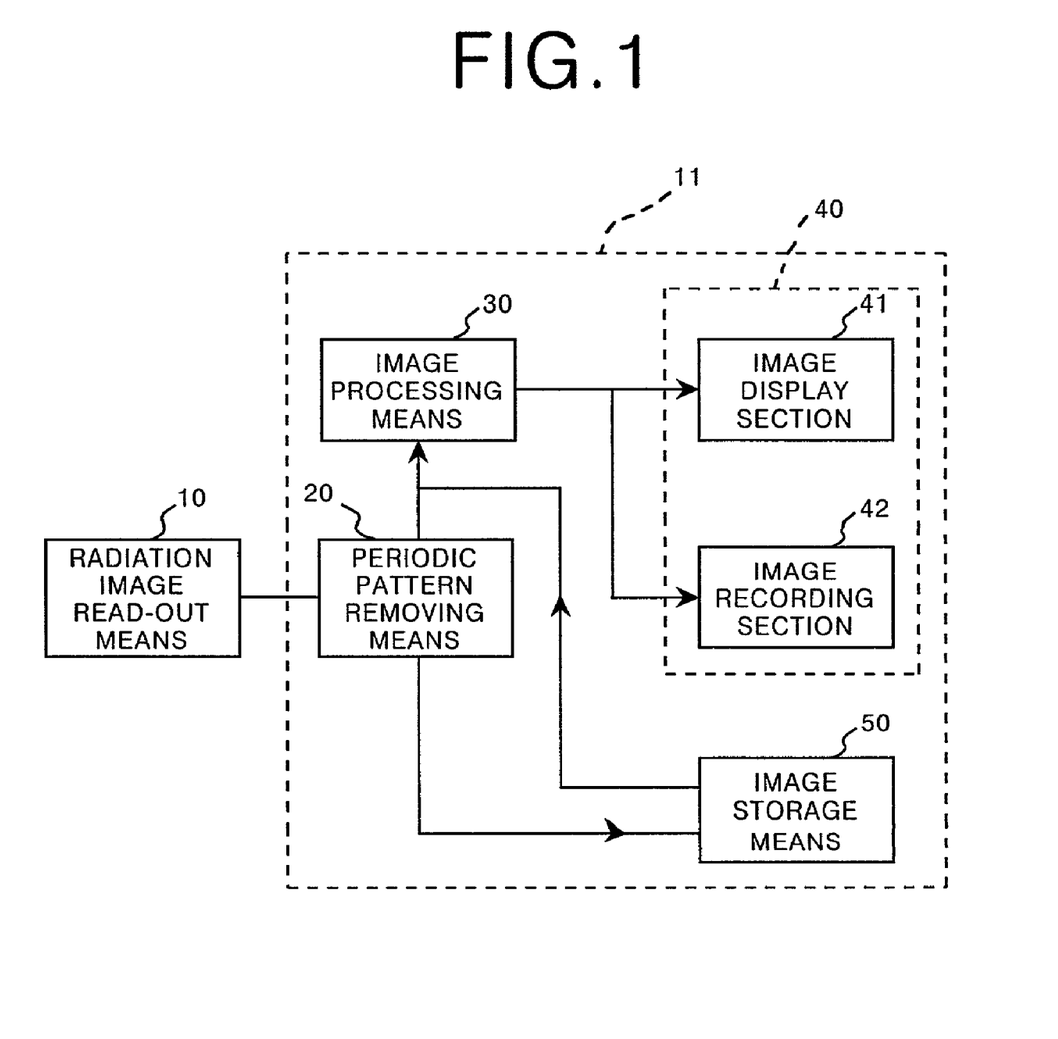
FIG. 1 is a block diagram showing a radiation image reproducing system in accordance with a first embodiment of the present invention.

In FIG. 1, the radiation image reproducing system 11 of this embodiment comprises a periodic pattern removing means 20 which carries out a grid removing processing (to be described later) on original image data read out by a radiation image read-out means 10 to remove a grid image therefrom and generates storage image data, an image storage means 50 which stores the storage image data output from the periodic pattern removing means 20, an image processing means 30 which carries out an enlargement/reduction processing on the storage image data output from the periodic pattern removing means 20 and generates output image data, and an image output means 40 comprising an image display section 41 for reproducing an image as display on a screen on the basis of the output image data and an image recording section 42 for reproducing as a hard copy on a predetermined recording medium such as a photographic film on the basis of the output image data.

In this particular embodiment, the radiation image read-out means 10 reads out a radiation image recorded on a stimulable phosphor sheet 7 (FIG. 2) in the following manner.

Figure 2:
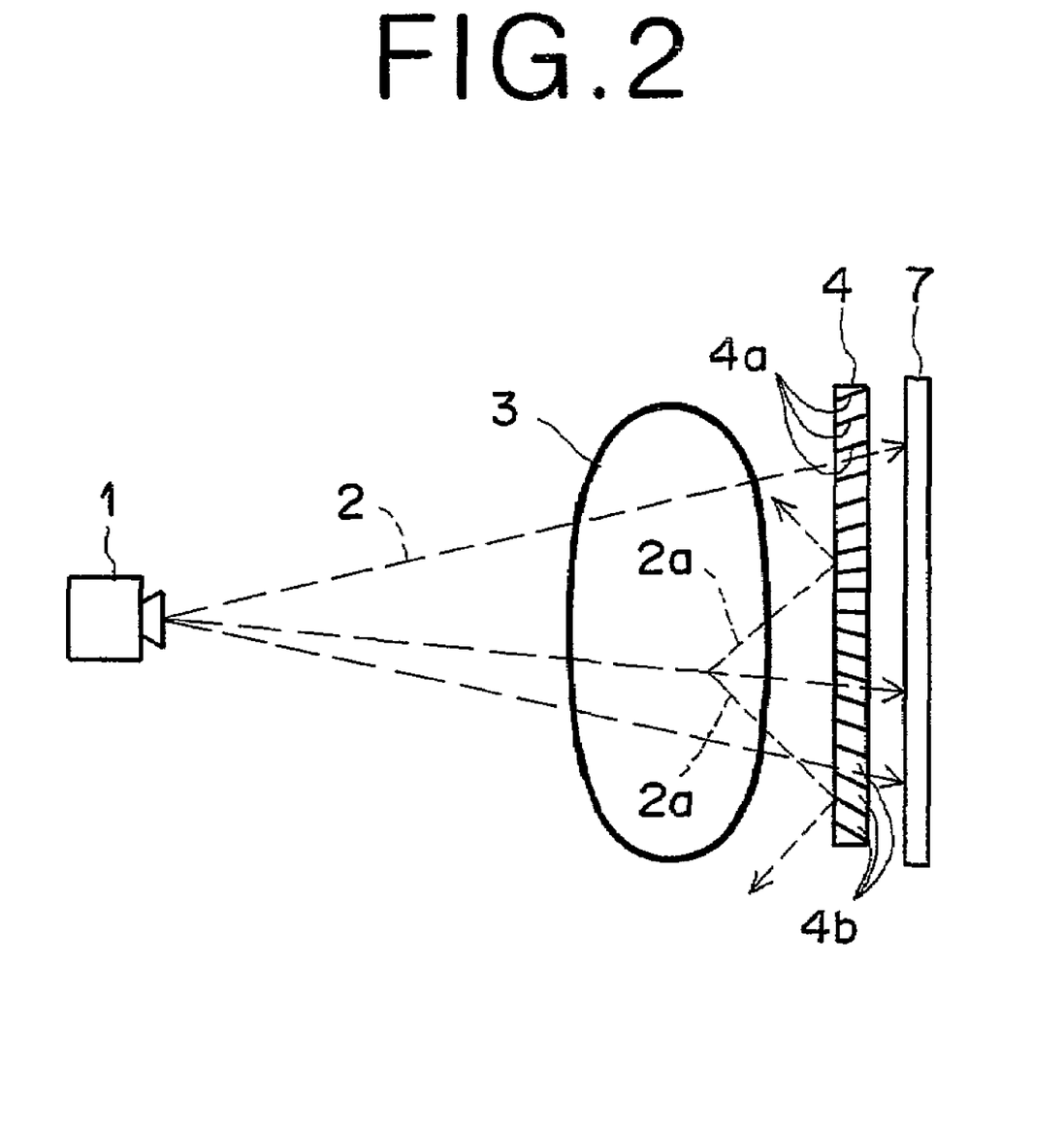
FIG. 2 is a schematic view showing an example of a radiation image taking apparatus.

A radiation 2 radiated from a radiation source 1 is projected onto a stimulable phosphor sheet 7 through an object 3 and a stationary grid 4. The stationary grid 4 comprises linear lead members 4a and linear aluminum members which are alternately arranged at pitches of 4/mm. The radiation 2 is cut by the lead members 4a and passes through the aluminum members 4b to be projected onto the stimulable phosphor sheet 7. Accordingly, an image of the grid 4 is recorded on the stimulable phosphor sheet 7 together with a radiation image of the object 3. Radiation 2a scattered in the object 3 obliquely impinges upon the grid 4 and accordingly is partly cut by the grid 4 and partly reflected by the grid 4, whereby the scattered radiation can hardly impinge upon the stimulable phosphor sheet 7 and a sharp radiation image free from influence of the scattered radiation is recorded on the stimulable phosphor sheet 7. The spatial frequency of the grid image is 4 cycles/mm.

Figure 3:
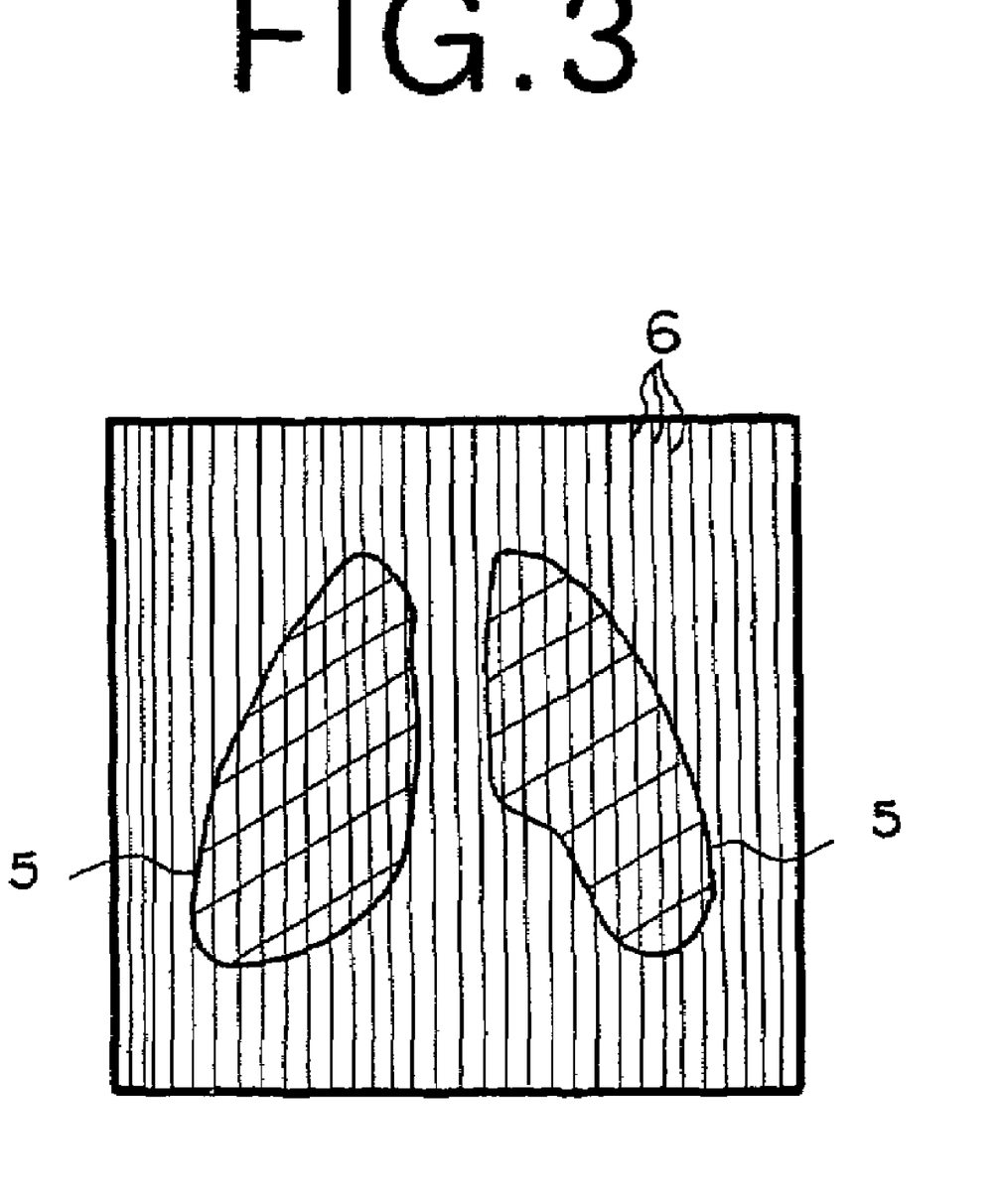
FIG. 3 is a view showing an example of a radiation image taken by the use of a grid.

FIG. 3 shows a radiation image recorded on the stimulable phosphor sheet 7 by the use of the grid 4, where an image 6 of the grid 4 (marked by the vertical stripes) is superposed on a radiation image 5 of the object 3 (marked by the oblique stripes).

Figure 4:
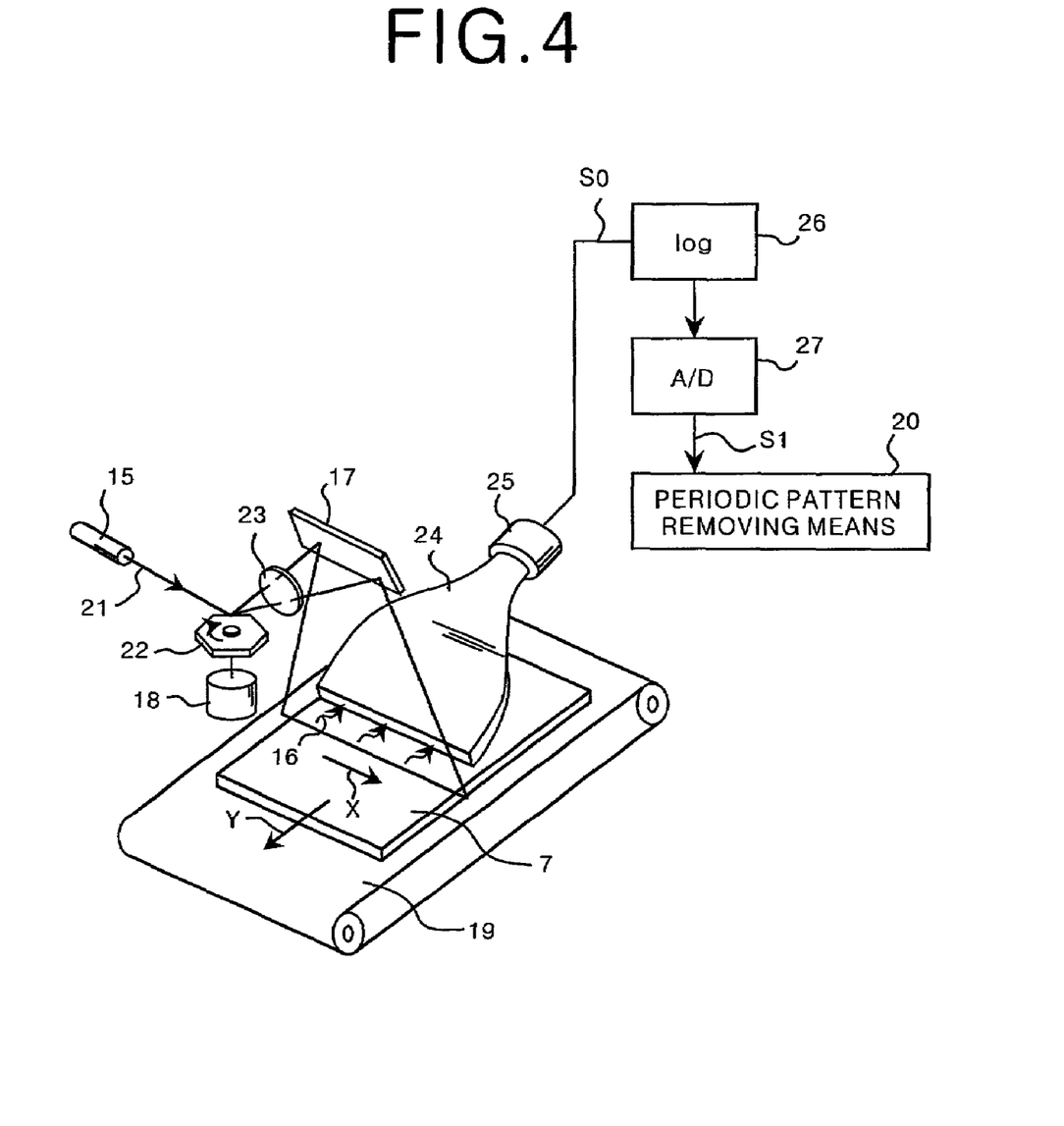
FIG. 4 is a perspective view showing an example of a radiation image read-out means.

The radiation image read-out means 10 will be described with reference to FIG. 4, hereinbelow.

The stimulable phosphor sheet 7 which has been exposed to the radiation 2 through the object 3 is conveyed by a sheet conveyor means 19 (which may be an endless belt) driven by a driving means (not shown) in the direction of arrow Y (sub-scanning). The stimulable phosphor sheet 7 is set on the sheet conveyor means 19 so that the stimulable phosphor sheet 7 is conveyed in perpendicular to the grid image 6. While the stimulable phosphor sheet 7 is being conveyed by the sheet conveyor means 19 in the direction of arrow Y, a laser beam 21 emitted from a laser 20 is caused to scan the stimulable phosphor sheet 7 in a main scanning direction (the direction of arrow X) substantially perpendicular to the sub-scanning direction by a scanning optical system comprising a rotary polygonal mirror 22 driven by a motor 18 to rotate at high speed in the direction of the arrow, a condenser lens 23 (which may be an fθ lens) and a mirror 17. In this particular embodiment, the read-out density of the radiation image read-out means 10 in the main scanning direction can be switched between 10 pixels/mm and 5 pixels/mm. Since the stationary grid is generally 3.4/mm, 4/mm, 6/mm or 8/mm in density (3.4 cycles/mm, 4 cycles/mm, 6 cycles/mm or 8 cycles/mm in spatial frequency), the Nyquist frequency is 2.5 cycles/mm. Accordingly, no grid image exists in original image data when the read-out density of the radiation image read-out means 10 is 5 pixels/mm. To the contrast, when the read-out density of the radiation image read-out means 10 is 10 pixels/mm, there exists a grid image in the original image data, and accordingly, it is necessary to carry out a grid removing processing in the image display means 30. The parts of the stimulable phosphor sheet 7 exposed to the laser beam 21 emits stimulated emission 16 in amounts proportional to the amounts of radiation energy stored therein. The stimulated emission 16 is led to a photomultiplier 25 by a light guide 24 and is photoelectrically detected by the photomultiplier 25, whereby the amounts of the stimulated emission 16 representing a radiation image of the object 3 are converted into an analog electric image signal S0.

The analog image signal S0 is logarithmically amplified by a logarithmic amplifier 26 and then sampled at 10 pixels/mm by an A/D convertor 27 to be digitized into a digital original image data S1. The original image data S1 is input into the image output means 40 and the image storage means 50 together with information on the read-out density as attendant information.

The periodic pattern removing means 20 in the radiation image reproducing system of this embodiment carries out a noise removing processing on the original image data S1 on the basis of the attendant information and generates storage image data.

The image storage means 50 in this particular embodiment is an image data server which stores the storage image data read out by the periodic pattern removing means 10. When the periodic pattern removing means 20 is arranged to output, together with the storage image data, information on whether the periodic pattern removing means 20 has carried out a noise removing processing on the original image data, the image storage means 50 stores also the information together with the storage image data related to each other.

Though basically being for displaying on the screen an image reproduced on the basis of the output image data obtained by carrying out an enlargement/reduction processing by the image processing means 30, the image display section 41 may display an image reproduced on the basis of the storage image data which has not been subjected to an enlargement/reduction processing, when enlargement or reduction of the original image is not necessary.

The image recording section 42 comprises a printer (not shown) which records an image reproduced on the basis of the original image data output from the image processing means 30 on a recording medium such as a photographic film. The image recording section 42 may record an image reproduced on the basis of the storage image data output from the periodic pattern removing means 20 or the image storage means 50.

It is possible to arrange the system so that the image processing means 30 is included in the image output means 40.

The operation of the radiation image reproducing system of this embodiment will be described, hereinbelow.

The original image data representing a radiation image recorded on the stimulable phosphor sheet 7 is read out by the radiation image read-out means 10 in the manner described above and input into the periodic pattern removing means 20. At this time, whether an image is to be reproduced by the image display section 41 as display on the basis of output image data or to be reproduced by the image recording means 42 as a hard copy on the basis of output image data is selected through an input means (not shown).

At this time, the attendant information on the read-out density is input into the periodic pattern removing means 20 together with the original image data. The periodic pattern removing means 20 carries out the noise removing processing on the original image data when the read-out density of the radiation image read-out means 10 is 10 pixels/mm and outputs the original image data removed with the noise to the image processing means 30 and the image storage means 50 as storage image data. Whereas, when the read-out density of the radiation image read-out means 10 is 5 pixels/mm, the periodic pattern removing means 20 outputs the original image data as it is to the image processing means 30 and the image storage means 50 as storage image data without carrying out the noise removing processing. The image processing section 30 carries out an enlargement processing or a reduction processing at a predetermined rate of enlargement or reduction and outputs the resultant image data to the image output means 40 as output image data.

When that an image is to be reproduced by the image display section 41 as display, the output image data is input into the image display section 41 and the image display section 41 displays an image on the basis of the output image data.

When that an image is to be reproduced by the image recording section 42 as a hard copy is selected, the output image data is input into the image recording section 42 and the image recording section 42 prints by the printer an image reproduced on the basis of the output image data.

A plurality of rates of enlargement or reduction may be set in advance in the image processing means 30 so that the image processing means 30 creates a plurality of pieces of output image data obtained by enlarging or reducing the storage image data at the rates of enlargement or reduction set in advance and a plurality of images are reproduced on the basis of plurality of pieces of output image data at one time on a screen or a sheet of recording medium. One or more rates of enlargement or reduction other than the rates of enlargement or reduction set in advance in the image processing means 30 may be input into the image processing means 30 through an input means (not shown) or when the storage image data is provided with attendant information representing the rate of enlargement of reduction at which the radiation image is to be enlarged or reduced, the rate of enlargement or reduction represented by the attendant information may be input into the image processing means 30.

The output image data output from the periodic pattern removing means 20 is input into the image storage means 50. At this time, when the storage image data is provided with information on whether the storage image data has been removed with noise, the image storage means 50 stores the storage image data in combination with the information. That is, when the original image is read out by the radiation image read-out means 10 at 10 pixels/mm, storage image data removed with a grid image is stored in the image storage means 50 together with information representing that the storage image data has been subjected to a noise removing processing and when the original image is read out by the radiation image read-out means 10 at 5 pixels/mm, storage image data is stored in the image storage means 50 together with information representing that the storage image data has not been subjected to a noise removing processing.

The storage image data thus stored in the image storage means 50 can be output to the image processing means 30 to be enlarged and or reduced and can be output as a reproduced image from the image output means 40 at any time in response to a predetermined input signal from an input means (not shown).

When the storage image data is provided with information representing that the storage image data has been subjected to a noise removing processing, character(s) or sign(s) representing the fact may be displayed or recorded so that diagnosis can be made more accurately taking into the condition of the image displayed or recorded.

In the image reproduction system in accordance with the first embodiment of the present invention, the original image data is removed with noise of periodic pattern to generate storage image data, the storage image data is stored in the image storage means 50, output image data is generated by carrying out an enlargement/reduction processing on the storage image data read out from the image storage means 50 and a reproduced image is output on the basis of the output image data. Accordingly, an image free from moiré fringes can be constantly output from either of the image display section 41 and the image recording section 42. Further, since the periodic pattern removing means 20 can be common to the image display section 41 and the image recording section 42, cost can be reduced.

A radiation image reproducing system in accordance with a second embodiment of the present invention will be described with reference to FIG. 5, hereinbelow. In the second embodiment, the elements analogous to those in the first embodiment will be given the same reference numerals and will not be described here.

Figure 5:
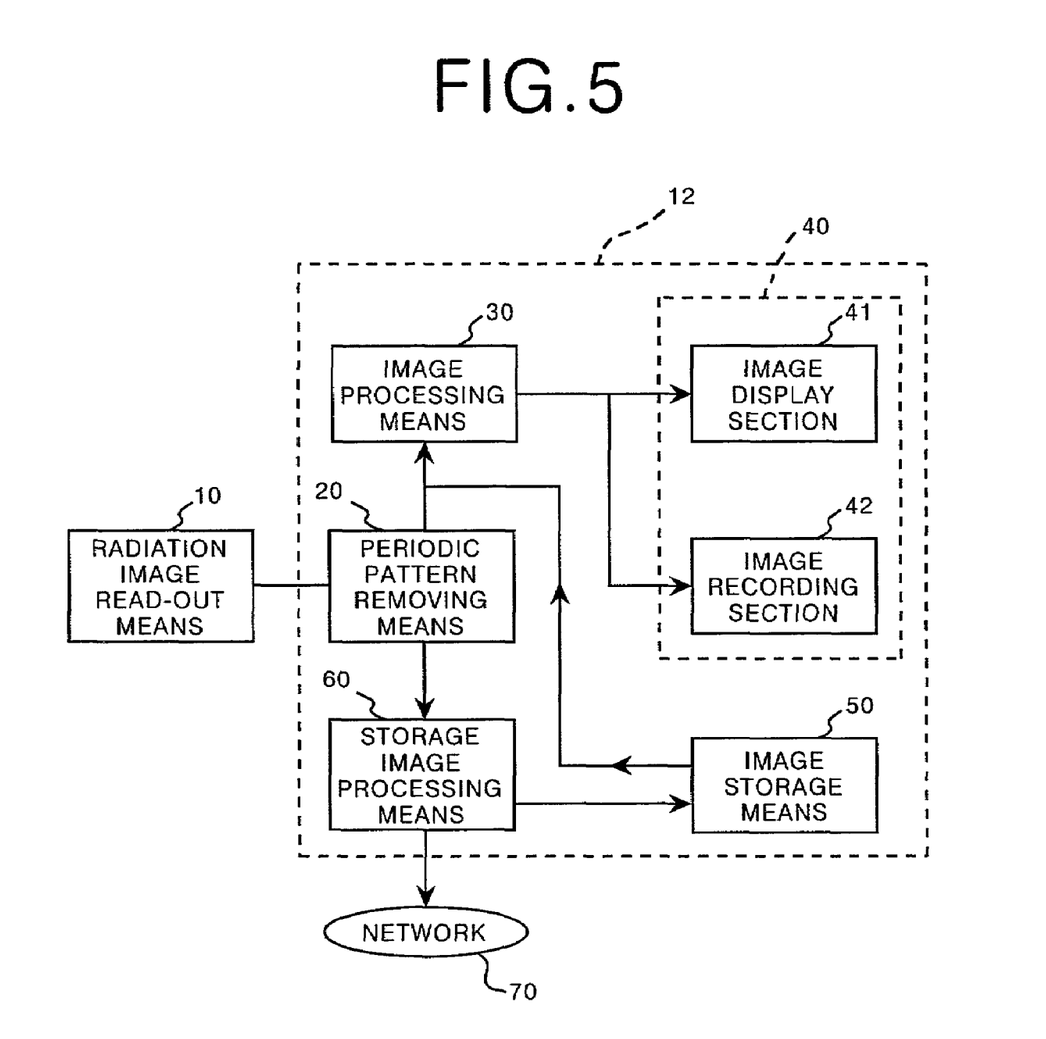
FIG. 5 is a block diagram showing a radiation image reproducing system in accordance with a second embodiment of the present invention.

In FIG. 5, the radiation image reproducing system 12 of this embodiment comprises a periodic pattern removing means 20 which carries out a noise removing processing on original image data read out by a radiation image read-out means 10 and generates processed image data, a storage image processing means 60 which generates storage image data by converting the processed original image data, output from the periodic pattern removing means 20, to storage image data whose resolution is lower than that of the processed original image data, an image storage means 50 which stores the storage image data output from the storage image processing means 60, an output image processing means 30 which carries out an enlargement/reduction processing on the processed image data output from the periodic pattern removing means 20 or the storage image data stored in the image storage means 50 and generates output image data, and an image output means 40 comprising an image display section 41 for reproducing an image as display on a screen on the basis of the output image data output from the output image processing means 30 and an image recording section 42 for reproducing as a hard copy on a predetermined recording medium such as a photographic film on the basis of the output image data output from the output image processing means 30. The storage image processing means 60 is connected to a network 70 such as LAIN.

In this embodiment, the radiation image read-out means 10 reads out a radiation image recorded on a stimulable phosphor sheet 7 in the same manner as the first embodiment.

The storage image processing means 60 generates storage image data by converting the processed image data (obtained by carrying out a noise removing processing on the original image data by the periodic pattern removing means 20) to storage image data whose resolution is lower than that of the processed original image data by carrying out, for instance, a reduction processing on the processed original image data and outputs the storage image data thus obtained to the image storage means 50. Accordingly, the amount of the storage image data can be reduced, whereby the image storage means 50 can be small in capacity. The storage image data may be stored in the image storage means 50 after its amount of data is reduced not by reduction but, for instance, by compression.

The storage image data can be transferred to other image storage means or image output means by way of the network 70. At this time, since the storage image data is small in its amount of data, the storage image data can be transferred at high speed.

The operation of the radiation image reproducing system of this embodiment will be described, hereinbelow.

The original image data representing a radiation image recorded on the stimulable phosphor sheet 7 is read out by the radiation image read-out means 10 in the manner described above and input into the periodic pattern removing means 20. At this time, whether an image is to be reproduced by the image display section 41 as display on the basis of output image data or to be reproduced by the image recording means 42 as a hard copy on the basis of output image data is selected through an input means (not shown).

At this time, the attendant information on the read-out density is input into the periodic pattern removing means 20 together with the original image data from the radiation image read-out means 10. The periodic pattern removing means 20 carries out the noise removing processing on the original image data when the read-out density of the radiation image read-out means 10 is 10 pixels/mm and outputs the original image data removed with the noise to the output image processing means 30 and the storage image processing means 60 as processed image data. Whereas, when the read-out density of the radiation image read-out means 10 is 5 pixels/mm, the periodic pattern removing means 20 outputs the original image data as it is to the output image processing means 30 and the storage image processing means 60 as processed image data without carrying out the noise removing processing. The output image processing section 30 carries out an enlargement processing or a reduction processing at a predetermined rate of enlargement or reduction and outputs the resultant image data to the image output means 40 as output image data.

The storage image processing means 60 generates storage image data whose resolution is half of the processed image data output from the periodic pattern removing means 20 by carrying out, for instance, a reduction processing on the processed image data and outputs the storage image data to the image storage means 50 or the network 70.

The storage image data thus stored in the image storage means 50 can be output to the image processing means 30 to be enlarged and or reduced and can be output as a reproduced image from the image output means 40 at any time in response to a predetermined input signal from an input means (not shown). The image reproducing system of this embodiment is the same as that of the first embodiment in the other operation.

In the image reproduction system in accordance with the second embodiment of the present invention, the original image data is removed with the grid image to generate processed image data, storage image data is generated by converting the processed original image data to storage image data whose resolution is lower than that of the processed original image data and is stored in the image storage means 50, output image data is generated by carrying out an enlargement/reduction processing on the processed original image data and/or the storage image data, and a reproduced image is output on the basis of the output image data. Accordingly, the amount of the storage image data can be reduced, whereby the image storage means can be small in capacity, and at the same time, the storage image data can be transferred at high speed through the network 70. Such features can be obtained in addition to the features obtained in the image reproducing system of the first embodiment.

Though, in the first and second embodiments described above, the periodic pattern removing means 20 determines whether original image data is to be subjected to a noise removing processing on the basis of information on the read-out density output from the radiation image read-out apparatus 10, the periodic pattern removing means 20 may be arranged to automatically recognize whether a grid image exists in the original image and to carry out a noise removing processing only when it recognizes that there is a grid image in the original image, or may be arranged to receive a predetermined signal from a predetermined input means or imaging menu representing whether a grid image exists in the original image and to determine whether original image data is to be subjected to a noise removing processing on the basis of the predetermined signal or the imaging menu.

Whether a grid image exists in the original image can be automatically recognized, for instance, by sampling values of a predetermined number of pixels from the original image data, sampling a predetermined area of the image on the basis of the sampled values of the pixels and detecting a periodic pattern by carrying out a smoothening processing or a mathematical processing using an autocorrelation function on the image (see Japanese Unexamined Patent Publication No. 8(1996)-293020).

Further, it is possible to select one of three modes, in one mode a noise removing processing is carried out on the basis of input imaging menu, in another mode a noise removing processing is not carried out on the basis of input imaging menu, and in the other mode a noise removing processing is carried out on the basis of a grid image automatically recognized. For example, when the imaging menu represents that the object part is a hand or foot, no noise removing processing is carried out since no grid is used in taking a radiation image in such a case, when the imaging menu represents that the object part is a breast, no noise removing processing is carried out since a movable grid is used in taking a radiation image and no grid image appears in such a case, when the imaging menu represents that the object part is a lumber, only a noise removing processing for removing vertical noise is carried out since a vertical stationary grid is used in taking a radiation image in such a case, and when the imaging menu represents that the object part is a pelvis, a noise removing processing for removing horizontal noise since a horizontal stationary grid is used in taking a radiation image in such a case. When the object part is a part an image of which is rarely taken, a noise removing processing is carried out on the basis of the result of automatic grid image recognition.

By not carrying out a noise removing processing when no grid exists in the original image, information other than that on a grid image can be prevented from being lost from the original image.

By determining again, after the noise removing processing is carried out on the original image data, whether the original image data is to be subjected to a noise removing processing in response to input through a predetermined input means as described above, when the fact that the original image data has been accidentally removed with noise is revealed through the reproduced image, the error can be corrected.

It is possible to arrange the system so that the periodic pattern removing means 20 automatically recognizes the period and the direction of the periodic pattern and carries out a different noise removing processing according to the period and the direction of the periodic pattern automatically recognized. Further it is possible to arrange the system so that the noise removing processing is carried out in different ways according to the period and the direction of the periodic pattern represented by a signal input through a predetermined input means, an imaging menu, original image data or the like. Further, it is possible to arrange the system so that selection of a method of the noise removing processing on the basis of the period and the direction of the periodic pattern automatically recognized and selection of the same on the basis of information input thereinto can be switched.

The direction of the periodic pattern in the original image data can be detected, for instance, in the following manner. That is, in Fourier transform of image signal components for a pixel train extending in perpendicular to the linear periodic pattern in the original image data, the spatial frequency components of the linear periodic pattern appear as specific high peaks. Accordingly, the direction in which the specific high peaks do not appear, or the direction in which a pixel train whose peak power is smaller extend, may be considered to be the direction of a stationary grid. See, for instance, Japanese Unexamined Patent Publication No. 2(1990)-263279.

Further, when the system is arranged so that even after the original image data is subjected to the noise removing processing determined in the manner described above, the original image data can be subjected to another noise removing processing in response to input through a predetermined input means, when the fact that the original image data has been accidentally removed with noise by a wrong noise removing processing is revealed through the reproduced image, the error can be corrected.

Further, when the noise removing processing carried out on original image data is to be corrected as desired (including the case where no noise removing processing has been carried out on the original image data and the case where the noise removing processing which has been carried out on the original image data is to be cancelled), it is preferred that a storage medium such as a memory in which the original image data is temporarily stored for a predetermined time or until a predetermined signal is input through a predetermined input means so that the original image data is read out from the storage medium and can be subjected to another noise removing processing.

When the system is arranged so that the original image data is deleted from the storage medium immediately after the noise removing processing in the case where it is not necessary to correct the noise removing processing, the capacity of the storage medium need not be large.

Further, it is preferred that the processed original image data output from the periodic pattern removing means 20 to the image processing means 30 be lower in resolution than the original image data as read out by the radiation image read-out means 10. By this, the enlargement/reduction processing in the image processing means 30 can be performed at high speed as well other processing, e.g., an enhancement processing or a gradation processing. The processed original image data may be equal in resolution to the monitor of the image display section 41.

Though, in the embodiment described above, the original image data representing an original image is obtained by reading out an image recorded on a recording medium (a stimulable phosphor sheet in the particular embodiment), the original image data may be obtained directly from a solid state radiation image sensor or the like.

What is claimed is:

1. An image reproduction system comprising an image output means which outputs a reproduced image on the basis of an original image data representing an original image, wherein the improvement comprises that there are provided:
    a periodic pattern removing means which carries out on the original image data a noise removing processing to remove noise of a predetermined periodic pattern, if any, from the original image data and generates storage image data,
    an image storage means which stores the storage image data,
    an output image processing means which carries out an enlargement/reduction processing on the storage image data read out from the image storage means and generates output image data,
    and the image output means outputs a reproduced image on the basis of the output image data,
    wherein the original image data is provided with information representing imaging menu and the periodic pattern removing means carries out a noise removing processing on the original image data according to the imaging menu represented by the information, and
    further comprising a determining means for determining whether periodic pattern removal is necessary in the original image data;
    wherein the determining means determines there is a predetermined periodic pattern in the original image data when the determining means receives information pertaining to a first read-out density, readings per unit length, of a corresponding image read-out means, and
    wherein the periodic removing means determines that there is no predetermined periodic pattern in the original image data when the determining means receives information pertaining to a second read-out density, readings per unit length, of the image read-out means.

2. An image reproduction system comprising an image output means which outputs a reproduced image on the basis of an original image data representing an original image, wherein the improvement comprises that there are provided:
    a periodic pattern removing means which carries out on the original image data a noise removing processing to remove noise of a predetermined periodic pattern, if any, from the original image data and generates storage image data,
    an image storage means which stores the storage image data,
    an output image processing means which carries out an enlargement/reduction processing on the storage image data read out from the image storage means and generates output image data,
    and the image output means outputs a reproduced image on the basis of the output image data,
    wherein the original image data is provided with information representing imaging menu and the periodic pattern removing means carries out a noise removing processing on the original image data according to the imaging menu represented by the information, and
    wherein an image read-out means transmits information pertaining to a first read-out density to the periodic pattern removing means and the periodic pattern removing means transmits the storage image data together with information identifying whether the storage image data has been removed of the noise to the image storage means.

3. An image reproduction system as defined in claim 1, wherein the determining means determines whether to remove a predetermined periodic pattern in the original image data based on the anatomical structure of the original image data.

4. An image reproduction system comprising an image output means which outputs a reproduced image on the basis of an original image data representing an image read out from an original, wherein the improvement comprises that there are provided
    a periodic pattern removing means which carries out on the original image data a noise removing processing to remove noise of a predetermined periodic pattern, if any, from the original image data and generates processed original image data,
    a storage image processing means which generates storage image data by converting the processed original image data to storage image data whose resolution is lower than that of the processed original image data,
    an image storage means which stores the storage image data and
    an output image processing means which carries out an enlargement/reduction processing on the processed original image data and/or the storage image data and generates output image data, and the image output means outputs a reproduced image on the basis of the output image data, wherein the original image data is provided with information representing imaging menu and the periodic pattern removing means carries out a noise removing processing on the original image data according to the imaging menu represented by the information, and further comprising a determining means for determining whether periodic pattern removal is necessary in the original image data;

wherein the determining means determines there is a predetermined periodic pattern in the original image data when the determining means receives information pertaining to a first read-out density, readings per unit length, of a corresponding image read-out means, and wherein the periodic removing means determines that there is no predetermined periodic pattern in the original image data when the determining means receives information pertaining to a second read-out density, readings per unit length, of the image read-out means.

5. An image reproduction system comprising an image output means which outputs a reproduced image on the basis of an original image data representing an image read out from an original, wherein the improvement comprises that there are provided a periodic pattern removing means which carries out on the original image data a noise removing processing to remove noise of a predetermined periodic pattern, if any, from the original image data and generates processed original image data, a storage image processing means which generates storage image data by converting the processed original image data to storage image data whose resolution is lower than that of the processed original image data, an image storage means which stores the storage image data and an output image processing means which carries out an enlargement/reduction processing on the processed original image data and/or the storage image data and generates output image data, and the image output means outputs a reproduced image on the basis of the output image data, wherein the original image data is provided with information representing imaging menu and the periodic pattern removing means carries out a noise removing processing on the original image data according to the imaging menu represented by the information, and wherein an image read-out means transmits information pertaining to a first read-out density to the periodic pattern removing means and the periodic pattern removing means transmits the processed original image data to the storage image processing means.

6. An image reproduction system as defined in claim 5, wherein the storage image processing means transmits the storage image data to the image storage means.

7. An image reproduction system as defined in claim 5, wherein the storage image processing means transmits the storage image data to a local area network.

8. An image reproduction system comprising an image output means which outputs a reproduced image on the basis of an original image data representing an original image, wherein the improvement comprises that there are provided a periodic pattern removing means which carries out on the original image data a noise removing processing to remove noise of a predetermined periodic pattern, if any, from the original image data and generates storage image data, an image storage means which stores the storage image data, an output image processing means which carries out an enlargement/reduction processing on the storage image data read out from the image storage means and generates output image data, and the image output means outputs a reproduced image on the basis of the output image data, and a determining means for determining whether periodic pattern removal is necessary in the original image data;

wherein the determining means determines there is a predetermined periodic pattern in the original image data when the determining means receives information pertaining to a first read-out density, readings per unit length, of a corresponding image read-out means, and wherein the periodic removing means determines that there is no predetermined periodic pattern in the original image data when the determining means receives information pertaining to a second read-out density, readings per unit length, of the image read-out means.

9. An image reproduction system comprising an image output means which outputs a reproduced image on the basis of an original image data representing an original image, wherein the improvement comprises that there are provided a periodic pattern removing means which carries out on the original image data a noise removing processing to remove noise of a predetermined periodic pattern, if any, from the original image data and generates storage image data, an image storage means which stores the storage image data, an output image processing means which carries out an enlargement/reduction processing on the storage image data read out from the image storage means and generates output image data, and the image output means outputs a reproduced image on the basis of the output image data, and an image read-out means which transmits information pertaining to a first read-out density to the periodic pattern removing means and the periodic pattern removing means transmits the storage image data together with information identifying whether the storage image data has been removed of the noise to the image storage means.

* * * * *